US012588904B2

(12) United States Patent
Wohlert

(10) Patent No.: US 12,588,904 B2
(45) Date of Patent: Mar. 31, 2026

(54) IMPLANT DEVICES AND FABRICATION METHODS FOR IMPLANT DEVICES

(71) Applicant: Miach Orthopaedics, Inc., Westborough, MA (US)

(72) Inventor: Stephen Wohlert, Westborough, MA (US)

(73) Assignee: Miach Orthopaedics, Inc., Westborough, MA (US)

( * ) Notice: Subject to any disclaimer, the term of this patent is extended or adjusted under 35 U.S.C. 154(b) by 387 days.

(21) Appl. No.: 17/854,007

(22) Filed: Jun. 30, 2022

(65) Prior Publication Data

US 2023/0000482 A1     Jan. 5, 2023

Related U.S. Application Data

(60) Provisional application No. 63/217,197, filed on Jun. 30, 2021.

(51) Int. Cl.
    *A61B 17/04*          (2006.01)
(52) U.S. Cl.
    CPC .. *A61B 17/0401* (2013.01); *A61B 2017/0414* (2013.01); *A61B 2017/0464* (2013.01)
(58) Field of Classification Search
    CPC ........ A61B 17/0401; A61B 2017/0414; A61B 2017/0464; A61B 2017/00526; A61B 2017/1132; A61B 17/1146; A61L 27/3633; A61L 27/24; A61L 27/3662; A61F 2002/087; A61F 2230/0069; A61F 2240/004; A61F 2/08
    See application file for complete search history.

(56) References Cited

U.S. PATENT DOCUMENTS 6,280,474 B1 *   8/2001   Cassidy ................. B29C 48/12
                                                                606/232
9,561,027 B2     2/2017   Perriello et al.
                          (Continued)

FOREIGN PATENT DOCUMENTS

EP        3 753 497 A1     12/2020
WO     2007/087353 A2      8/2007
WO     2018/009637 A1      1/2018

OTHER PUBLICATIONS

International Search Report issued in International Patent Application No. PCT/US2022/035652 issued Oct. 19, 2022.

*Primary Examiner* — Richard G Louis
(74) *Attorney, Agent, or Firm* — Offit Kurman; Mary K Nicholes

(57)                    ABSTRACT

Technologies are disclosed for an implant device that may be configured to repair tissue. The device may include a distal end configured to be connectable to at least a first part of the tissue. The device may include a proximate end configured to be connectable to at least a second part of the tissue. The device may include a substrate configured to form a connection between the first part of the tissue and the second part of the tissue. The device may include a longitudinal axis that may extend between the distal end to the proximate end within the substrate. The device may include at least one preformed channel in the substrate. The device may include at least one suture preloaded at least partially within the at least one channel. The at least one preformed channel may be formed during and/or proximate to a formation of the device.

33 Claims, 8 Drawing Sheets

(56)          References Cited

U.S. PATENT DOCUMENTS

2005/0025514  A1       2/2005  Kitozaki
2012/0010634  A1*      1/2012  Crabb  ................ A61B 17/0057
                                                            606/232
2018/0125477  A1       5/2018  Stone
2020/0138422  A1*      5/2020  Hebert  ................... B29D 23/00

* cited by examiner

IMPLANT DEVICES AND FABRICATION METHODS FOR IMPLANT DEVICES

CROSS-REFERENCE TO RELATED APPLICATIONS

The present application claims priority to and the benefit of U.S. Provisional Patent Application No. 63/217,197, filed Jun. 30, 2021, the contents of which are hereby incorporated in their entirety.

BACKGROUND

Soft tissues, tendons, and/or ligaments can be damaged in the course of sporting activities, strenuous exercise, physically demanding work, and/or normal, everyday physical activities. However the damage is incurred, a subject who suffers such an injury may be limited, perhaps significantly, from engaging in employment functions, sporting activities, physical exercise, and/or some social engagements, etc.

Subjects with such injuries typically may seek surgical intervention to repair such damage. Anterior cruciate ligament (ACL), medial collateral ligament (MCL), Achilles tendon, meniscus, among other soft tissue, tendons, and/or ligaments may, or might not, naturally heal properly and/or fully. For example, naturally forming clots/scaffolds might not develop in a timely or structurally adequate fashion, if such clots/scaffolds develop at all.

Tissues found outside of joints heal by forming a fibrin clot, which connects the ruptured tissue ends and is subsequently remodeled to form scar, which heals the tissue. Inside a synovial joint, a fibrin clot either fails to form or is quickly lysed after injury to the knee, thus preventing joint arthrosis and stiffness after minor injury. Joints contain synovial fluid which, as part of normal joint activity, naturally prevent clot formation in joints. This fibrinolytic process results in premature loss of the fibrin clot scaffold and disruption of the healing process for tissues within the joint or within intra-articular tissues. Surgical treatments to repair such injuries/damages may include removing the damaged tissue and replacing the removed tissue with a point-to-point tissue graft.

SUMMARY

Technologies are disclosed for an implant device that may be configured to repair tissue. The device may comprise a distal end that may be configured to be connectable to at least a first part of the tissue. The device may comprise a proximate end that may be configured to be connectable to at least a second part of the tissue. The device may comprise a substrate that may be configured to form a connection between the first part of the tissue and the second part of the tissue. The device may comprise a longitudinal axis that may extend between the distal end to the proximate end within the substrate. The device may include at least one preformed channel in the substrate. The device may comprise at least one suture that may be preloaded at least partially within the at least one channel.

In one or more scenarios, the implant device may be configured such that the tissue for repair may be soft tissue, a tendon, and/or a ligament.

In one or more scenarios, the substrate may be constructed (e.g., partially and/or substantially) of collagen (e.g., human, porcine, bovine, equine, avian, piscine, etc.), and/or bovine connective tissue.

In one or more scenarios, the implant device may have a (e.g., partially and/or substantially) cylindrical shape, a (e.g., partially and/or substantially) oval shape, a (e.g., partially and/or substantially) round shape, a (e.g., partially and/or substantially) rectangular shape, a (e.g., partially and/or substantially) square shape, or a (e.g., partially and/or substantially) trapezoidal shape, among other shapes.

In one or more scenarios, the substrate may be constructed of one or more materials that may be saturable by human blood.

In one or more scenarios, the at least one preformed channel may be formed during a formation of the device, and/or (e.g., substantially) proximate in time to a post-formation processing of the device.

In one or more scenarios, the at least one suture may be a number two absorbable suture, or a number two non-absorbable suture.

In one or more scenarios, the at least one preformed channel may be disposed along the longitudinal axis in the center of the device. In one or more scenarios, the at least one preformed channel may comprise a first opening in the substrate. The device may comprise a second opening in the substrate. The first opening and/or the second opening may be configured to accommodate a transmission of the at least one suture through the at least one preformed channel.

In one or more scenarios, the first opening may be disposed (e.g., partially and/or substantially) in the center of the proximate end of the device. The second opening may be disposed (e.g., partially and/or substantially) in the center of the distal end of the device.

In one or more scenarios, the at least one preformed channel may be a first preformed channel. The device may comprise one or more of a second preformed channel, a third preformed channel, and/or a fourth preformed channel.

In one or more scenarios, the first preformed channel may comprise a first opening in the substrate and/or a second opening in the substrate. The second preformed channel may comprise a third opening in the substrate and/or a fourth opening in the substrate. The third preformed channel may comprise a fifth opening in the substrate and/or a sixth opening in the substrate. The fourth preformed channel may comprise a seventh opening in the substrate and/or an eighth opening in the substrate.

In one or more scenarios, the at least one preloaded suture may be a first preloaded suture. The device may comprise a second suture that may be preloaded at least partially within the second preformed channel. The device may comprise a third suture that may be preloaded at least partially within the third preformed channel. The device may comprise a fourth suture that may be preloaded at least partially within the fourth preformed channel.

In one or more scenarios, the first opening and/or the second opening may be configured at least to accommodate a transmission of the first suture through the first preformed channel. The third opening and/or the fourth opening may be configured at least to accommodate a transmission of the second suture through the second preformed channel. The fifth opening and/or the sixth opening may be configured at least to accommodate a transmission of the third suture through the third preformed channel. The seventh opening and/or the eighth opening may be configured at least to accommodate a transmission of the fourth suture through the fourth preformed channel.

In one or more scenarios, the first opening in the substrate may be disposed in a first quadrant of the proximate end at a penetration angle ranging between zero to forty-five degrees relative to the longitudinal axis. The second opening in the substrate may be disposed in a first quadrant of the distal end at a penetration angle ranging between zero to forty-five degrees relative to the longitudinal axis. The third opening in the substrate is disposed in a second quadrant of the proximate end at a penetration angle ranging between zero to forty-five degrees relative to the longitudinal axis. The fourth opening in the substrate may be disposed in a second quadrant of the distal end at a penetration angle ranging between zero to forty-five degrees relative to the longitudinal axis.

In one or more scenarios, the fifth opening in the substrate may be disposed in a third quadrant of the proximate end at a penetration angle ranging between zero to forty-five degrees relative to the longitudinal axis. The sixth opening in the substrate may be disposed in a third quadrant of the distal end at a penetration angle ranging between zero to forty-five degrees relative to the longitudinal axis. The seventh opening in the substrate may be disposed in a fourth quadrant of the proximate end at a penetration angle ranging between zero to forty-five degrees relative to the longitudinal axis. The eighth opening in the substrate may be disposed in a fourth quadrant of the distal end at a penetration angle ranging between zero to forty-five degrees relative to the longitudinal axis.

In one or more scenarios, the first preformed channel, the second preformed channel, the third preformed channel, and/or the fourth preformed channel may have a trajectory within the substrate that may be (e.g., partially and/or substantially) straight, (e.g., partially and/or substantially) diagonal, and/or or (e.g., partially and/or substantially) spiral, among other trajectories.

In one or more scenarios, the first opening in the substrate may be disposed in a first half of the proximate end at a penetration angle ranging between zero to forty-five degrees relative to the longitudinal axis. The second opening in the substrate may be disposed in a first half of the distal end at a penetration angle ranging between zero to forty-five degrees relative to the longitudinal axis. The third opening in the substrate may be disposed in a second half of the proximate end at a penetration angle ranging between zero to forty-five degrees relative to the longitudinal axis. The fourth opening in the substrate may be disposed in a second half of the distal end at a penetration angle ranging between zero to forty-five degrees relative to the longitudinal axis.

In one or more scenarios, implant devices with different numbers of preformed channels than those illustrated in the figures can be derived from the description herein and fall within the scope of this disclosure. For example, implant devices with three, five, six, seven, and/or eight, etc., preformed channels can be readily understood as being within the scope of the description herein. In one or more scenarios, a target number of preformed channels that may be evenly divided by two may be useful. In one or more scenarios, the size of the implant device and/or the size/number of sutures may inform the target number of preformed channels, for example.

In one or more scenarios, implant devices with different numbers of preloaded sutures than those illustrated in the figures can be derived from the description herein and fall within the scope of this disclosure. For example, implant devices with fewer or more preloaded sutures than a number of performed channels can be readily understood as being within the scope of the description herein. In one or more scenarios, a target number of preloaded sutures that provides for at least one preloaded suture per performed channel may be useful. In one or more scenarios, the size of the implant device and/or the size/number of sutures may inform the target number of preloaded sutures and/or a target preloaded sutures per preformed channel, for example.

An implant device to repair tissue may be fabricated using one or more methods. One or more methods may comprise providing an (e.g., injection) mold. The mold may have an internal space. One or more methods may comprise installing one or more needle-like elements in the internal space. The needle-like elements may (e.g., each) have a first end extending outside the internal space. One or more methods may comprise injecting/adding a substrate-forming material into the internal space. The one or more needle-like elements may provide one or more negative formation void spaces in the internal space. One or more methods may comprise removing the formed substrate from the mold. One or more methods may comprise processing the formed substrate to form the implant device. The one or more negative formation void spaces may provide one or more preformed channels in the implant device. The one or more preformed channels may be configured to accommodate transmission of one or more sutures through the one or more preformed channels.

One or more methods may comprise attaching one or more sutures to the first end of the one or more needle-like elements. In one or more methods, the removing the formed substrate from the mold may comprise drawing the one or more sutures through the one or more preformed channels. The one or more drawn-through sutures may provide the implant device with one or more preloaded sutures.

One or more methods to fabricate an implant device may comprise providing an (e.g., injection) mold. The mold having an internal space. One or more methods may comprise injecting/adding a substrate-forming material into the internal space. One or more methods may comprise inserting one or more needle-like elements into the substrate-forming material. The one or more needle-like elements may create one or more negative formation void spaces in the substrate-forming material. The one or more needle-like elements may have a first end extending outside the internal space. One or more methods may comprise removing the formed substrate from the mold. One or more methods may comprise processing the formed substrate to form the implant device. The one or more negative formation void spaces may provide one or more preformed channels in the implant device. The one or more preformed channels may be configured to accommodate transmission of one or more sutures through the one or more preformed channels.

One or more methods may comprise attaching one or more sutures to the first end of the one or more needle-like elements. The removing the formed substrate from the mold may comprise drawing the one or more sutures through the one or more preformed channels. The one or more drawn-through sutures may provide the implant device with one or more preloaded sutures.

One or more methods to fabricate an implant device may comprise providing an (e.g., injection) mold. The mold may have an internal space. One or more methods may comprise injecting/adding a substrate-forming material into the internal space. One or more methods may comprise removing the formed substrate from the mold. One or more methods may comprise processing the formed substrate to form the implant device. One or more methods may comprise inserting one or more needle-like elements into the implant device. The one or more needle-like elements may (e.g., each) have a first end extending outside the implant device, perhaps for example when inserted into the implant device. The one or more needle-like elements may create one or more preformed channels in the implant device. The one or more preformed channels may be configured to accommodate transmission of one or more sutures through the one or more preformed channels.

One or more methods may comprise attaching one or more sutures to the first end of the one or more needle-like elements. One or more methods may comprise driving the one or more needle-like elements through the implant device. The one or more driven-through sutures may provide the implant device with one or more preloaded sutures.

One or more methods of repairing a subject's tissue with an implant device tensioning at least one preloaded suture at least partially disposed within at least one preformed channel of the implant device. The preformed channel may be configured to accommodate transmission of the at least one preloaded suture through the at least one preformed channel. One or more methods may comprise connecting a distal end of the implant device to at least a first part of the tissue via a first length of the at least one suture extending from the at least one channel at the distal end. One or more methods may comprise connecting a proximate end of the implant device to at least a second part of the tissue via a second length of the at least one suture extending from the at least one channel at the proximate end. The distal end and the proximate end may be connected by a substrate of the implant device. The substrate may be configured to form a connection between the first part of the tissue and the second part of the tissue.

One or more methods may comprise saturating the substrate with the subject's blood.

BRIEF DESCRIPTION OF DRAWINGS

The elements and other features, advantages and disclosures contained herein, and the manner of attaining them, will become apparent and the present disclosure will be better understood by reference to the following description of various examples of the present disclosure taken in conjunction with the accompanying drawings, wherein.

DETAILED DESCRIPTION

Figure 1:
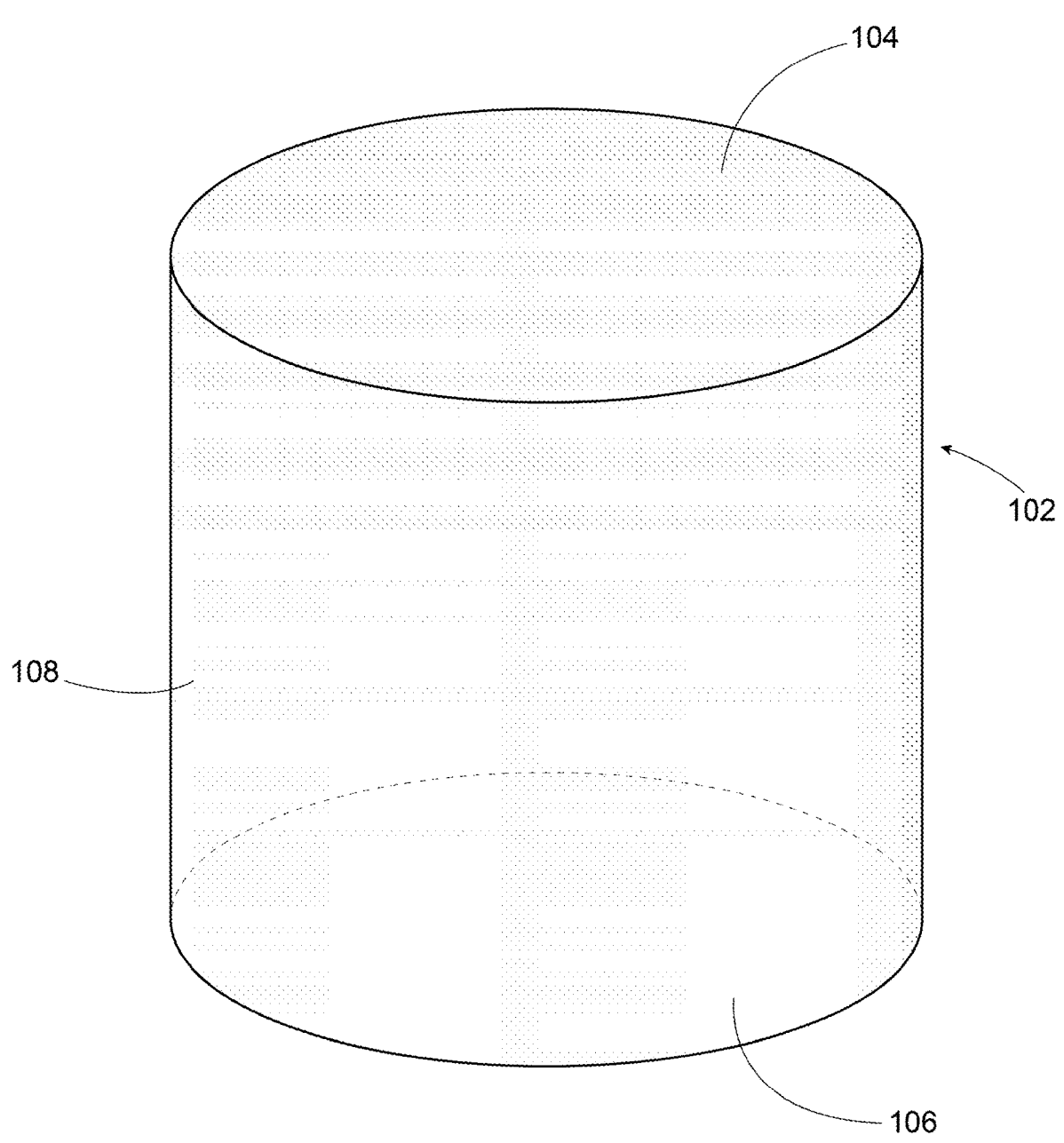
FIG. 1 is an example illustration of an implant device corresponding with subject matter described herein.

For the purposes of promoting an understanding of the principles of the present disclosure, reference will now be made to the examples illustrated in the drawings, and specific language will be used to describe the same. It will nevertheless be understood that no limitation of the scope of this disclosure is thereby intended.

Technologies are described herein for an implant device that may be configured to repair tissue. FIG. 1 is an example illustration of an implant device. Referring to FIG. 1, the implant device 102 may comprise a distal end 104 that may be configured to be connectable to at least a first part of the tissue (not shown). The device may comprise a proximate end 106 that may be configured to be connectable to at least a second part of the tissue (not shown). The device may comprise a substrate 108 that may be configured to form a connection between the first part of the tissue and the second part of the tissue. The implant device 102 may comprise a longitudinal axis that may extend between the distal end to the proximate end within the substrate.

The substrate 108 may be porous and/or may absorb blood. The implant device 102 may immobilize the autologous blood in the tissue wound site. The subject's blood may (e.g., naturally) form a clot and/or a (e.g., provisional) scaffold. The implant device 102 may protect the clot and/or maintain the clot within the tissue wound site. The blood clot may release wound healing growth factors and/or proteins that may aid in healing the damaged tissue. The implant device 102 may keep the blood in the tissue wound site and/or may protect the blood from being prematurely washed away.

The implant device 102 may include at least one preformed channel (not shown) in the substrate 108. The implant device 102 may comprise at least one suture (not shown) that may be preloaded at least partially within the at least one channel. In one or more scenarios, the implant device 102 may be configured such that the tissue for repair may be soft tissue, a tendon, and/or a ligament, among other tissues, for example.

In one or more scenarios, the substrate 108 may be constructed (e.g., partially and/or substantially) of collagen (e.g., human, porcine, bovine, equine, avian, piscine, etc.), bovine (e.g., subdermal) connective tissue, and/or extracellular matrix proteins, for example. In one or more scenarios, the substrate 108 may be constructed of one or more materials that may be saturable by human blood (e.g., the subject's blood, such as 10 milliliters (ml)). Although sizing may vary for various reasons, an example implant device 102 and/or substrate 108 may be approximately 45 millimeters (mm) in length along the longitudinal axis and approximately 22 mm in diameter.

In one or more scenarios, the implant device 102 may have a (e.g., partially and/or substantially) cylindrical shape, a (e.g., partially and/or substantially) oval shape (not shown), a (e.g., partially and/or substantially) round shape (not shown), a (e.g., partially and/or substantially) rectangular shape (not shown), a (e.g., partially and/or substantially) square shape (not shown), or a (e.g., partially and/or substantially) trapezoidal shape (not shown), among other shapes.

Technologies that may provide for one or more preformed channels in the implant device 102, and/or an implant device 102 with one or more preformed channels, such that surgical sutures may be transmitted through the one or more preformed channels, for example, may be useful. For example, one or more preformed channels in the implant device 102 may facilitate the insertion/loading of the surgical sutures through the implant device 102 that may be used to connect the implant device 102 to damaged tissue. The one or more preloaded channels may facilitate avoidance of damage to the implant device 102 during a loading of sutures without the one or more preloaded channels.

Technologies that may provide for the preloading of one or more sutures in the implant device 102, and/or an implant device 102 with one or more preloaded sutures, for example, may be useful. For example, one or more sutures at least partially preloaded in the implant device 102 may facilitate the connection of the implant device 102 to the damaged tissue, for example. The one or more preloaded sutures may facilitate avoidance of damage to the implant device 102 and/or to sutures during a loading of sutures without the one or more preloaded sutures.

In one or more scenarios, the at least one preformed channel (not shown) may be formed during a formation of the implant device 102, and/or (e.g., substantially) proximate in time to a post-formation processing of the implant device 102. In one or more scenarios, the at least one suture (not shown) may be a number two (#2) absorbable suture, or a number two (#2) non-absorbable suture. For example, #2 Ethibond sutures may be used, among other types and/or sizes of sutures.

Figure 4:
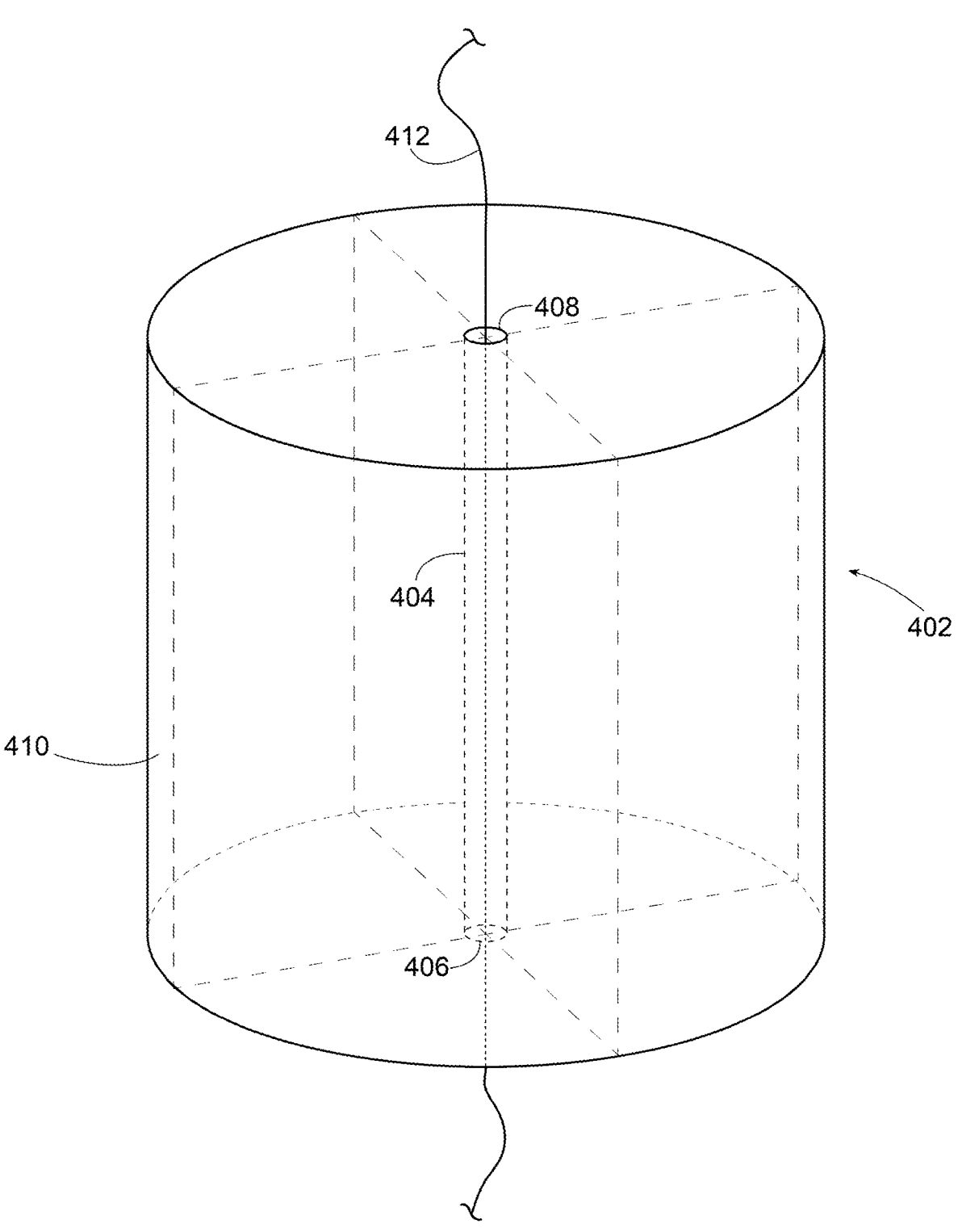
FIG. 4 is an example illustration of an implant device with at least one preformed channel corresponding with subject matter described herein.

FIG. 4 is an example illustration of an implant device with at least one preformed channel. Referring to FIG. 4, in one or more scenarios, the at least one preformed channel 404 may be disposed along the longitudinal axis in the center of the implant device 402. In one or more scenarios, the at least one preformed channel 404 may comprise a first opening 406 in the substrate 410. The implant device 402 may comprise a second opening 408 in the substrate 410. The first opening 406 and/or the second opening 408 may be configured to accommodate a transmission of the at least one suture 412 through the at least one preformed channel 404.

In one or more scenarios, the first opening 406 may be disposed (e.g., partially and/or substantially) in the center of a proximate end of the implant device 406. The second opening 408 may be disposed (e.g., partially and/or substantially) in the center of a distal end of the implant device 408.

Figure 2:
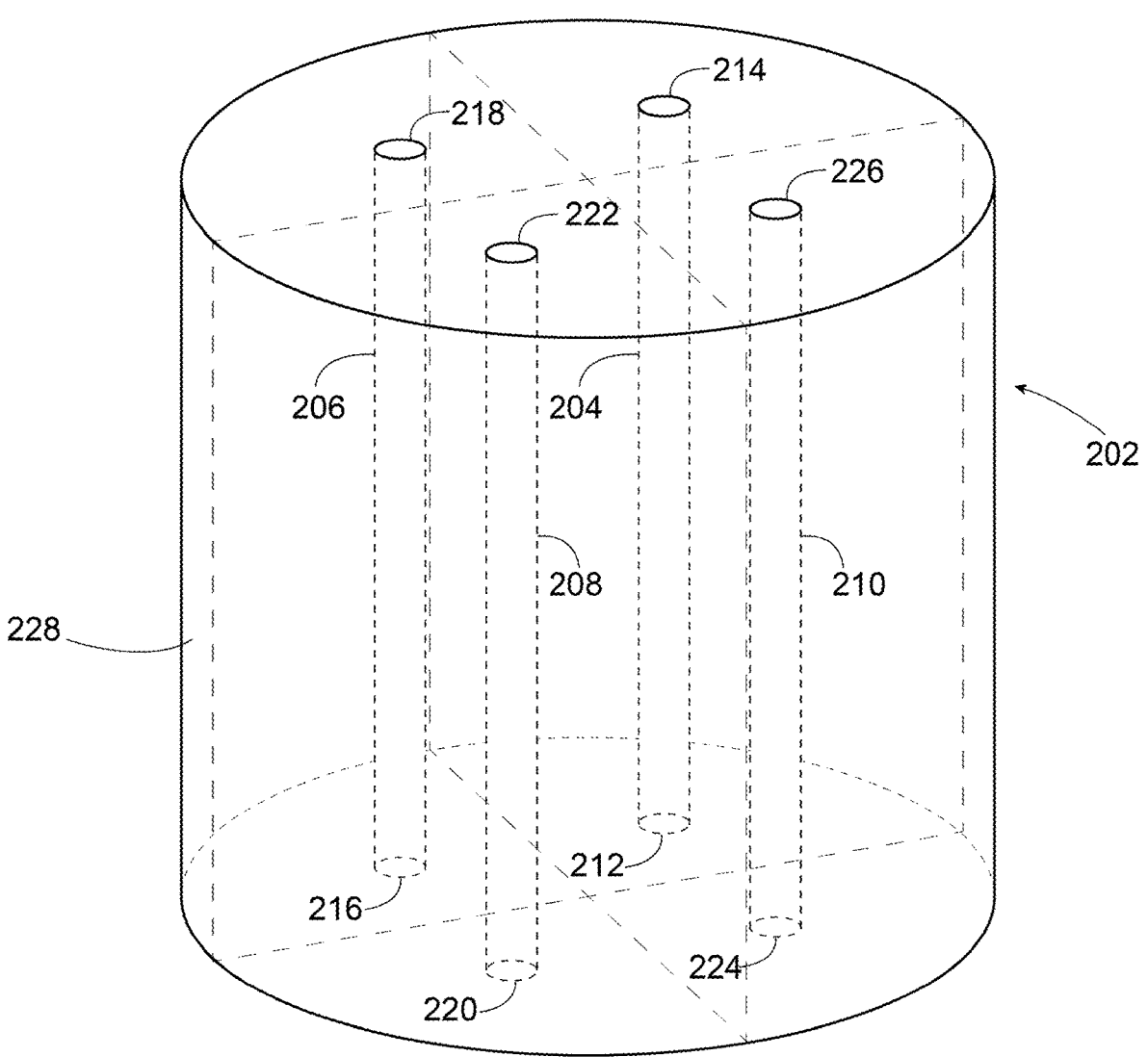
FIG. 2 is an example illustration of an implant device with at least four preformed channels corresponding with subject matter described herein.

FIG. 2 is an example illustration of an implant device with at least four preformed channels. Referring to FIG. 2, in one or more scenarios, the at least one preformed channel may be a first preformed channel 204. The device may comprise one or more of a second preformed channel 206, a third preformed channel 208, and/or a fourth preformed channel 210.

In one or more scenarios, the first preformed channel 204 may comprise a first opening 212 in the substrate 228 and/or a second opening 214 in the substrate 228. The second preformed channel 206 may comprise a third opening 216 in the substrate 228 and/or a fourth opening 218 in the substrate 228. The third preformed channel 208 may comprise a fifth opening 220 in the substrate 228 and/or a sixth opening 222 in the substrate 228. The fourth preformed channel 210 may comprise a seventh opening 224 in the substrate 228 and/or an eighth opening 226 in the substrate 228.

Figure 3:
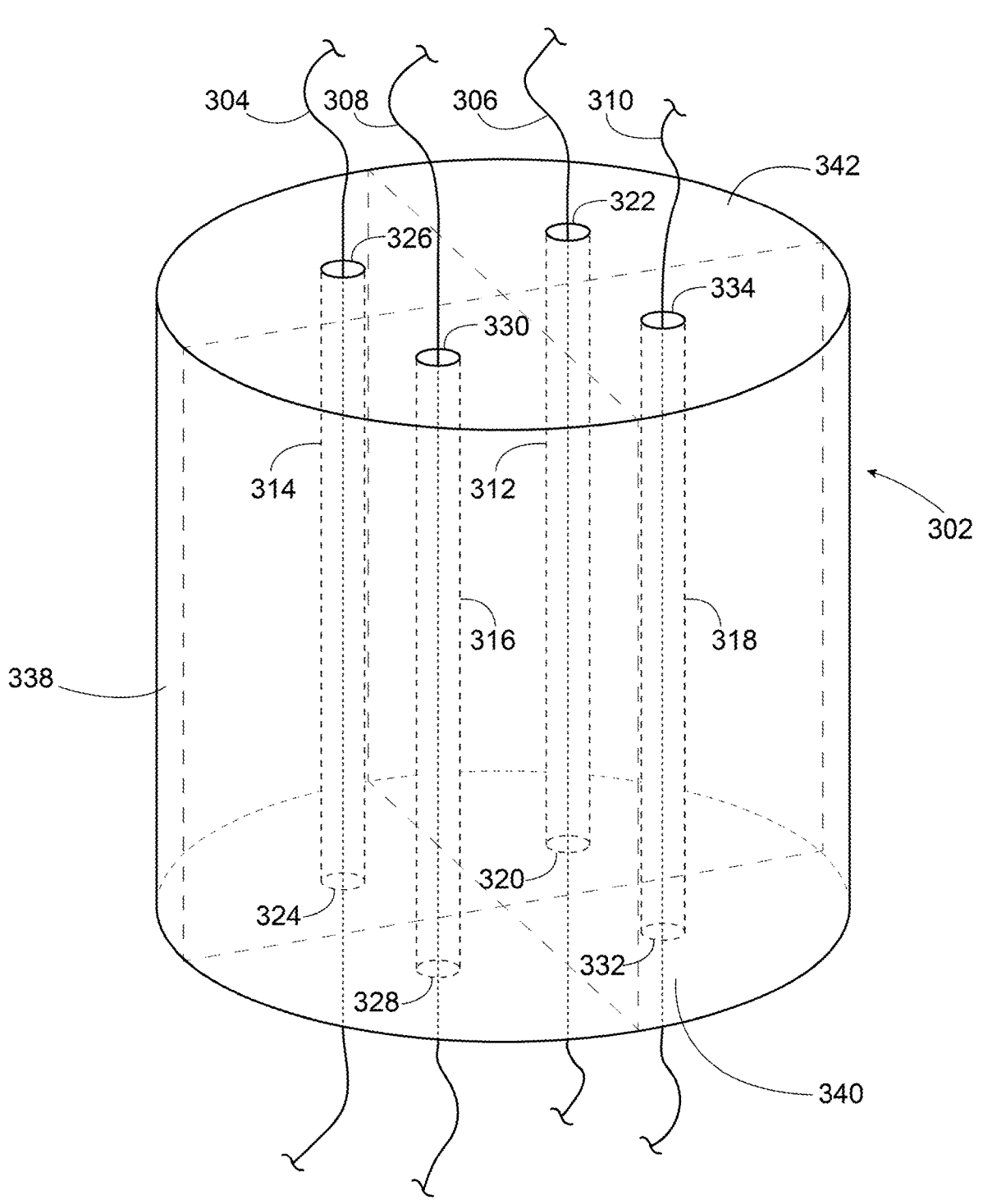
FIG. 3 is an example illustration of an implant device with one or more preformed channels and/or one or more preloaded sutures corresponding with subject matter described herein.

FIG. 3 is an example illustration of an implant device with one or more preformed channels and one or more preloaded sutures. In one or more scenarios, the at least one preloaded suture may be a first preloaded suture 306 that may be preloaded at least partially within the first preformed channel 312. The implant device 302 may comprise a second suture 304 that may be preloaded at least partially within the second preformed channel 314. The implant device 302 may comprise a third suture 308 that may be preloaded at least partially within the third preformed channel 316. The implant device 302 may comprise a fourth suture 310 that may be preloaded at least partially within the fourth preformed channel 318.

In one or more scenarios, the first opening 320 and/or the second opening 322 may be configured at least to accommodate a transmission of the first suture 306 through the first preformed channel 312. The third opening 324 and/or the fourth opening 326 may be configured at least to accommodate a transmission of the second suture 304 through the second preformed channel 314. The fifth opening 328 and/or the sixth opening 330 may be configured at least to accommodate a transmission of the third suture 308 through the third preformed channel 316. The seventh opening 332 and/or the eighth opening 334 may be configured at least to accommodate a transmission of the fourth suture 310 through the fourth preformed channel 318.

In one or more scenarios, the first opening 320 in the substrate 338 may be disposed in a first quadrant of a proximate end 340 at a penetration angle ranging between zero to forty-five degrees relative to the longitudinal axis (not shown). The second opening 322 in the substrate 338 may be disposed in a first quadrant of the distal end 342 at a penetration angle ranging between zero to forty-five degrees relative to the longitudinal axis. The third opening 324 in the substrate 338 may be disposed in a second quadrant of the proximate end 340 at a penetration angle ranging between zero to forty-five degrees relative to the longitudinal axis. The fourth opening 326 in the substrate 338 may be disposed in a second quadrant of the distal end 342 at a penetration angle ranging between zero to forty-five degrees relative to the longitudinal axis.

In one or more scenarios, the fifth opening 328 in the substrate 338 may be disposed in a third quadrant of the proximate end 340 at a penetration angle ranging between zero to forty-five degrees relative to the longitudinal axis. The sixth opening 330 in the substrate 338 may be disposed in a third quadrant of the distal end 342 at a penetration angle ranging between zero to forty-five degrees relative to the longitudinal axis. The seventh opening 332 in the substrate 338 may be disposed in a fourth quadrant of the proximate end 340 at a penetration angle ranging between zero to forty-five degrees relative to the longitudinal axis. The eighth opening 334 in the substrate may be disposed in a fourth quadrant of the distal end 342 at a penetration angle ranging between zero to forty-five degrees relative to the longitudinal axis.

In one or more scenarios, the first preformed channel 312, the second preformed channel 314, the third preformed channel 316, and/or the fourth preformed channel 318, and/or any of the preformed channels described and/or illustrated herein may have a trajectory within the substrate that may be (e.g., partially and/or substantially) straight, (e.g., partially and/or substantially) diagonal (not shown), and/or or (e.g., partially and/or substantially) spiral (not shown), among other trajectories.

Figure 5:
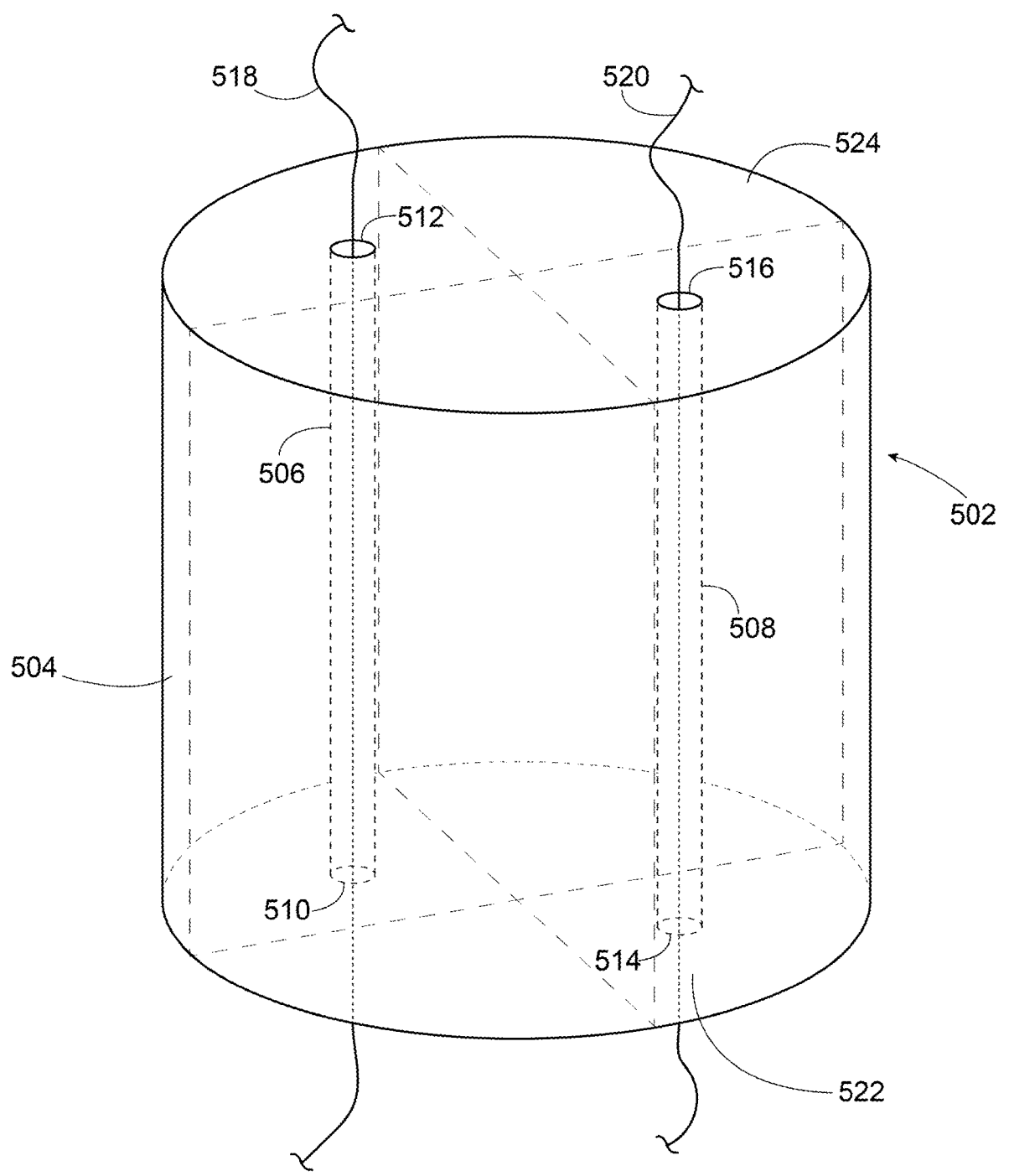
FIG. 5 is an example illustration of an implant device with at least two preformed channels corresponding with subject matter described herein.

FIG. 5 is an example illustration of an implant device with at least two preformed channels. Referring to FIG. 5, in one or more scenarios, implant device 502 may include a first preformed channel 506 and a second preformed channel 508 in a substrate 504. In one or more scenarios, a first opening 510 in the substrate 504 may be disposed in a first half of the proximate end 522 at a penetration angle ranging between zero to forty-five degrees relative to a longitudinal axis of the implant device 502 and/or substrate 504. second opening 512 in the substrate 504 may be disposed in a first half of the distal end 524 at a penetration angle ranging between zero to forty-five degrees relative to the longitudinal axis. A third opening 514 in the substrate 504 may be disposed in a second half of the proximate end 522 at a penetration angle ranging between zero to forty-five degrees relative to the longitudinal axis. A fourth opening 516 in the substrate 504 may be disposed in a second half of the distal end 524 at a penetration angle ranging between zero to forty-five degrees relative to the longitudinal axis.

In one or more scenarios, the first opening 510 and/or the second opening 512 may be configured at least to accommodate a transmission of a first suture 518 through the first preformed channel 506. The third opening 514 and/or the fourth opening 516 may be configured at least to accommodate a transmission of a second suture 520 through the second preformed channel 508.

In one or more scenarios, implant devices with different numbers of preformed channels than those illustrated in the figures can be derived from the description herein and fall within the scope of this disclosure. For example, implant devices with three, five, six, seven, and/or eight, etc., preformed channels can be readily understood as being within the scope of the description herein. In one or more scenarios, a target number of preformed channels that may be evenly divided by two may be useful. In one or more scenarios, the size of the implant device and/or the size/number of sutures may inform the target number of preformed channels, for example.

In one or more scenarios, implant devices with different numbers of preloaded sutures than those illustrated in the figures can be derived from the description herein and fall within the scope of this disclosure. For example, implant devices with fewer or more preloaded sutures than a number of performed channels can be readily understood as being within the scope of the description herein. In one or more scenarios, a target number of preloaded sutures that provides for at least one preloaded suture per performed channel may be useful. In one or more scenarios, the size of the implant device and/or the size/number of sutures may inform the target number of preloaded sutures and/or a target preloaded sutures per preformed channel, for example.

Figure 6:
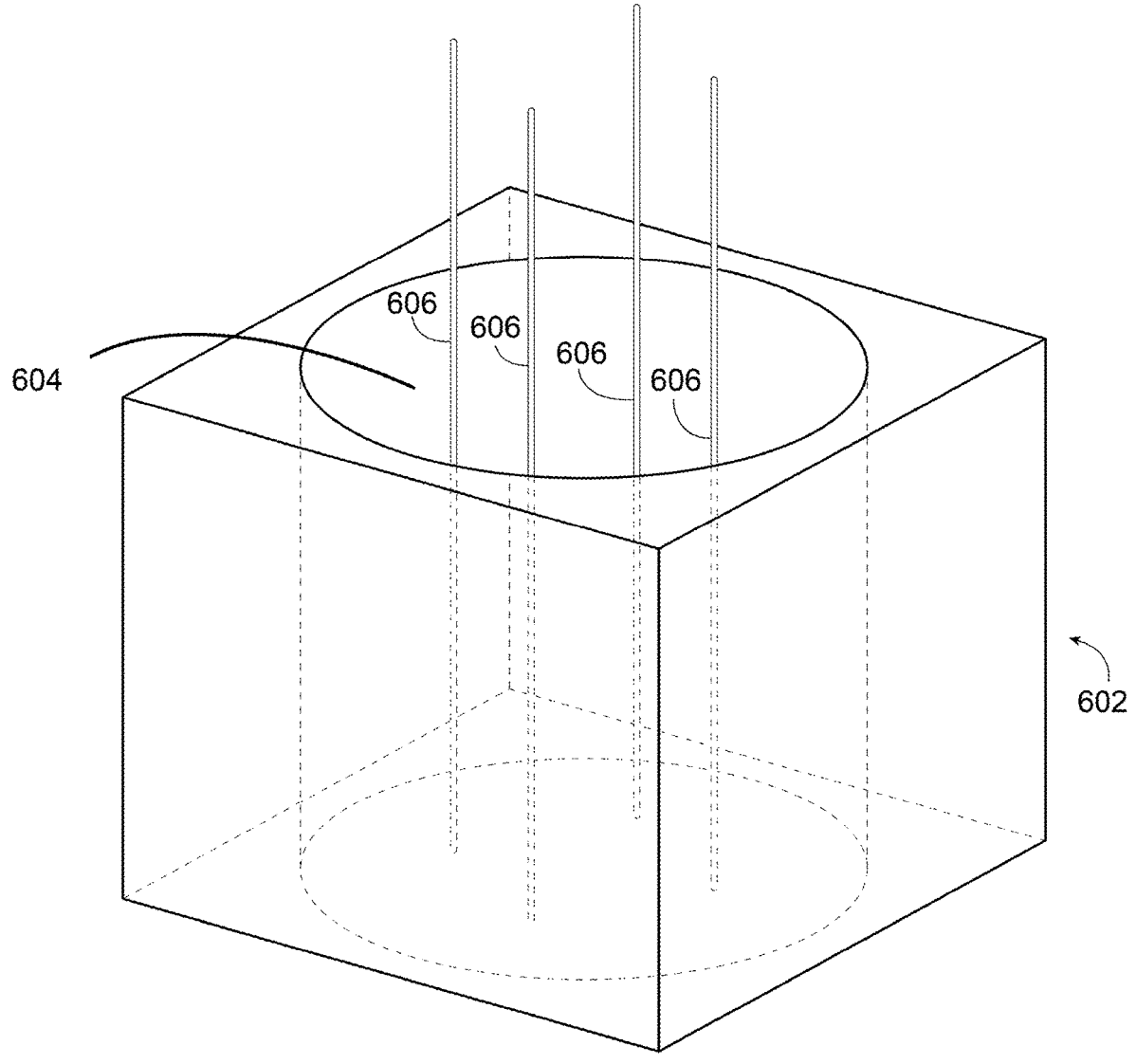
FIG. 6 is an example illustration of components used in a formation of an implant device with preformed channels corresponding with subject matter described herein.

FIG. 6 is an illustration of (e.g., injection) mold for formation of an implant device using one or more methods. Referring to FIG. 6, one or more methods may comprise providing an (e.g., injection) mold 602. The mold may have an internal space 604. One or more methods may comprise installing one or more needle-like elements 606 in the internal space 604. The needle-like elements 606 may (e.g., each) have a first end extending outside the internal space 604. One or more methods may comprise injecting/adding a substrate-forming material (not shown) into the internal space 604.

In one or more scenarios, the injecting/adding the substrate-forming material may be done with pressure, or without pressure (e.g., gravity fed), perhaps for example to speed up/control the injecting/adding/filling. The injecting/adding the substrate-forming material may be done at temperatures below 37° C., for example between 0° C. and 10° C. In one or more scenarios, the viscosity of substrate-forming material may inform injecting/adding/filling process.

The one or more needle-like elements 606 may provide one or more negative formation void spaces in the internal space 604. One or more methods may comprise processing (e.g., freezing, etc.) the formed substrate to form the implant device (not shown). In one or more scenarios, a viscosity of the substrate-forming material may be adjusted (e.g., increased to a "gel-like consistency, among other consistencies), for example by thermal treatment at 37° C. (e.g., between 20° C. to 40° C.) for a time such as two to four hours (e.g., between fifteen minutes and twelve hours). In one or more scenarios, the viscosity adjustment may be made based on other techniques include energy transfer into the mold 602 that result in heat energy that may increase the viscosity (e.g., "gelation", etc.).

In one or more scenarios, the processing may include lyophilization. The substrate-forming material may be frozen at −40° C. (e.g., between −8° C. to −60° C., perhaps for example based on collagen and/or salt content).

In one or more scenarios, the processing may include drying at −33° C. (e.g., between −10° C. and −60° C.), at 100 mTorr (e.g., between 1000 Torr and 5 mTorr), for 25 days (e.g., between 5 days and 45 days). The geometry of the implant may inform the processing. For example, for an implant device in an upright position, the processing may take longer and/or may utilize more "severe" conditions than for an implant device formed "lying on its side", among other orientations.

The one or more negative formation void spaces may provide one or more preformed channels (not shown) in the implant device. For example, the position and/or number of needle-like elements 606 may correspond to targeted position(s) and/or number of preformed channels in the implant device. The one or more preformed channels may be configured to accommodate transmission of one or more sutures (not shown) through the one or more preformed channels.

One or more methods may comprise removing the formed substrate (not shown) from the mold 602. In one or more scenarios, the formed substrate may be removed from the mold 602, for example by mechanically removing it from the mold 602 (e.g., pulling, pushing, dropping, splitting the mold 602, vacuum, etc.).

One or more methods may comprise attaching one or more sutures (not shown) to the first end of the one or more needle-like elements 606. In one or more methods, the removing the formed substrate from the mold 602 may comprise drawing the one or more sutures through the one or more preformed channels. The one or more drawn-through sutures may provide the implant device with one or more preloaded sutures (not shown).

Figure 7:
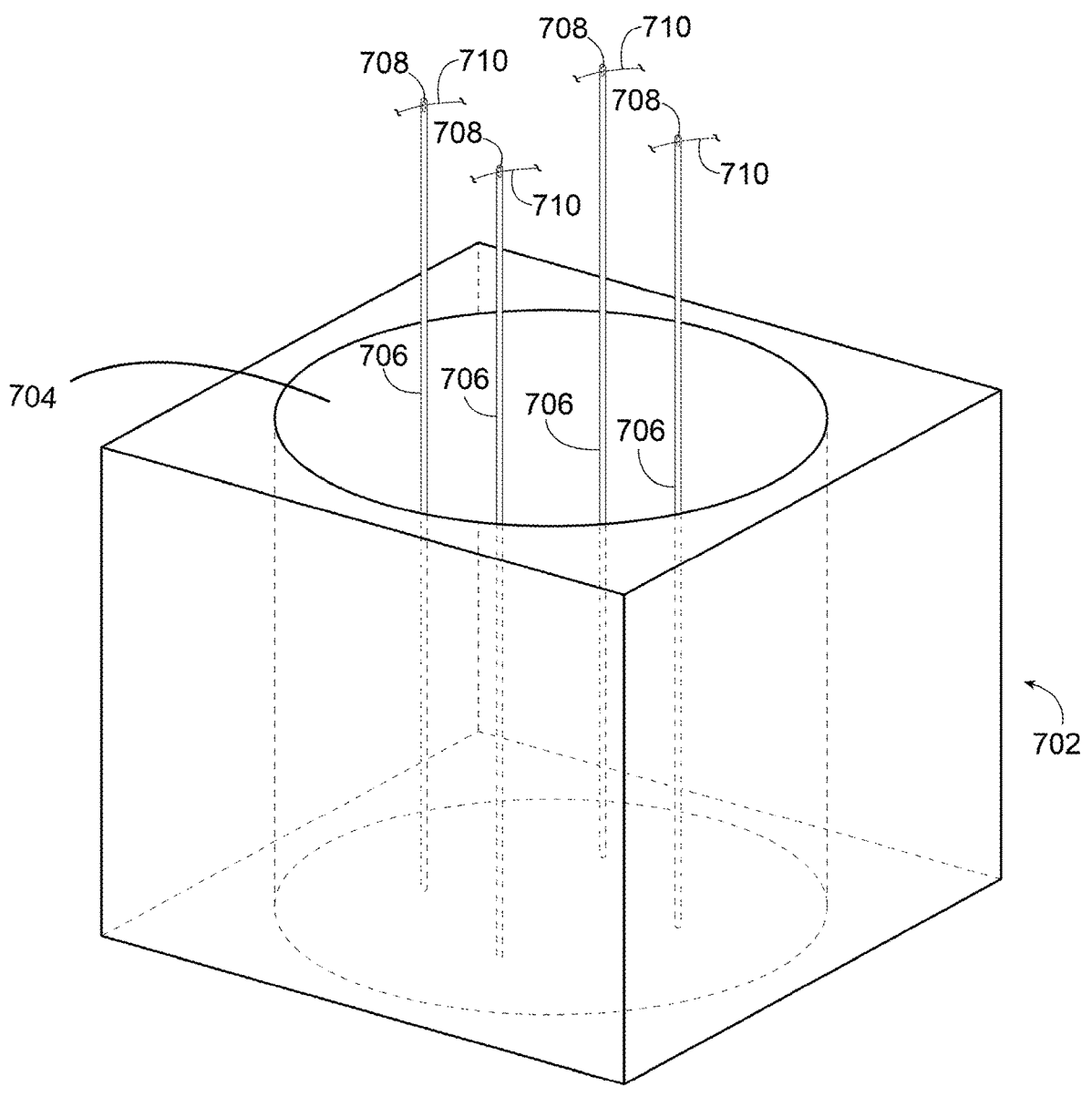
FIG. 7 is an example illustration of components used in a formation of an implant device with preformed channels corresponding with subject matter described herein.

FIG. 7 is an illustration of (e.g., injection) mold for formation of an implant device using one or more methods. Referring to FIG. 7, one or more methods may comprise providing an (e.g., injection) mold 702. The mold having an internal space 704. One or more methods may comprise injecting/adding a substrate-forming material (not shown) into the internal space 704. One or more methods may comprise inserting/adding one or more needle-like elements 706 into the substrate-forming material (e.g., as part of a lid to the mold 702). The one or more needle-like elements 706 may create one or more negative formation void spaces in the substrate-forming material. The one or more needle-like elements 706 may (e.g., each) have a first end extending outside the internal space 704.

In one or more scenarios, the one or more needle-like elements 706 may be inserted/added during the injecting/adding of the substrate-forming material (e.g., at the beginning, at the end, and/or during the filling). In one or more scenarios, the one or more needle-like elements 706 may be inserted/added during the viscosity adjustment (e.g., at the beginning, at the end, and/or during the viscosity adjustment). In one or more scenarios, the one or more needle-like elements 706 may be inserted/added (e.g., after) a lyophilization processing (e.g., as part of, or in addition to, freezing/drying processing, etc.).

One or more methods may comprise removing the formed substrate from the mold 702. One or more methods may comprise processing the formed substrate to form the implant device (not shown). The one or more negative formation void spaces may provide one or more preformed channels (not shown) in the implant device. For example, the position and/or number of needle-like elements 706 may correspond to targeted position(s) and/or number of pre-formed channels in the implant device. The one or more preformed channels may be configured to accommodate transmission of one or more sutures through the one or more preformed channels.

One or more methods may comprise attaching one or more sutures to the first end of the one or more needle-like elements 706. One or more (e.g., each) of the first ends may include an eyelet/orifice element 708 that may be configured to receive one or more sutures 710. In one or more scenarios, the removing the formed substrate from the mold 704 may comprise drawing (not shown) the one or more sutures 710 through the one or more preformed channels. The one or more drawn-through sutures may provide the implant device with one or more preloaded sutures (not shown).

Figure 8:
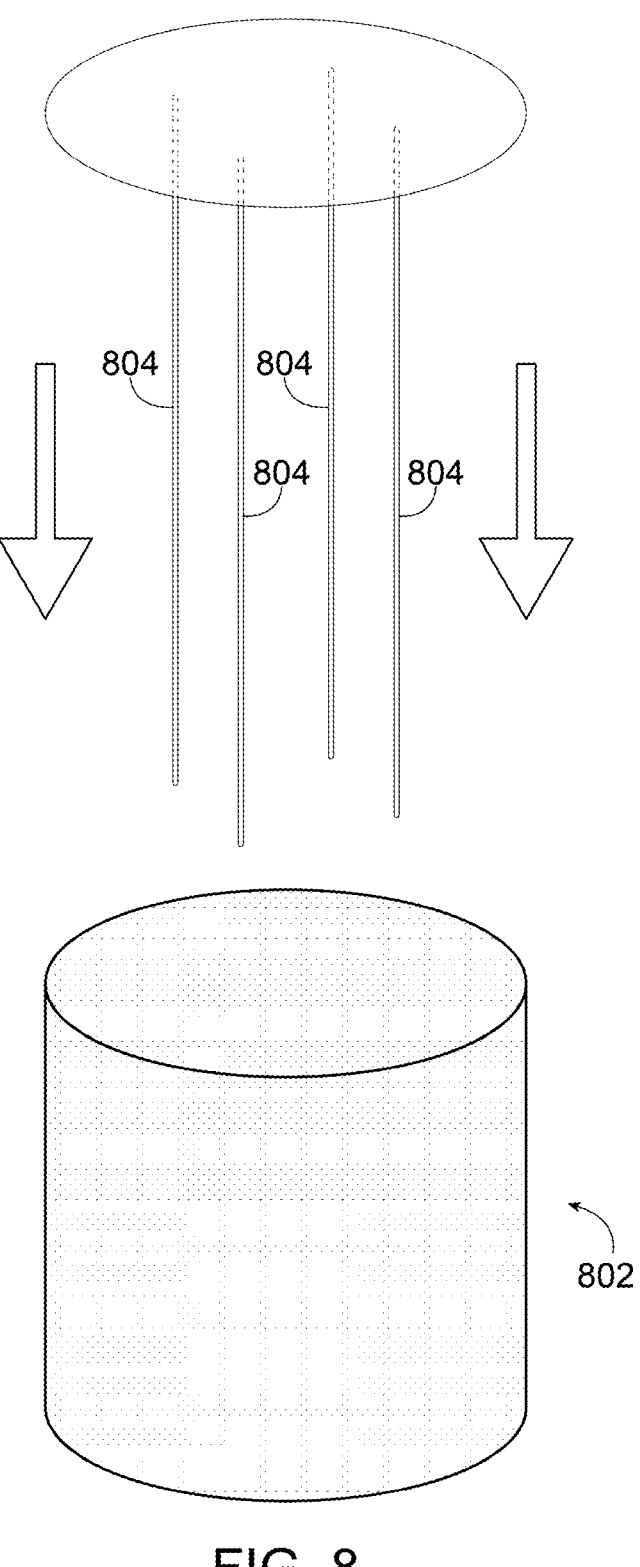
FIG. 8 is an example illustration of components used in a formation of an implant device with preformed channels corresponding with subject matter described herein.

FIG. 8 is an illustration of formation of an implant device using one or more methods. Referring to FIG. 8, one or more methods to fabricate an implant device 802 may comprise providing an (e.g., injection) mold (not shown). The mold may have an internal space (not shown). One or more methods may comprise injecting/adding a substrate-forming material (not shown) into the internal space. One or more methods may comprise removing the formed substrate (not shown) from the mold. One or more methods may comprise processing the formed substrate to form the implant device 802. One or more methods may comprise inserting one or more needle-like elements 804 into the implant device 802. The one or more needle-like elements 804 may (e.g., each) have a first end extending outside the implant device, perhaps for example when inserted (not shown) into the implant device 802. The one or more needle-like elements 804 may create one or more preformed channels (not shown) in the implant device 802. For example, the position and/or number of needle-like elements 804 may correspond to targeted position(s) and/or number of preformed channels in the implant device 802. The one or more preformed channels may be configured to accommodate transmission of one or more sutures through the one or more preformed channels.

One or more methods may comprise attaching one or more sutures (not shown) to the first end of the one or more needle-like elements. One or more methods may comprise driving (not shown) the one or more needle-like elements 804 through the implant device 802. The one or more driven-through sutures may provide the implant device with one or more preloaded sutures.

In one or more of the implant device fabrication methods described herein, the substrate-forming material may be a collagen-based material (e.g., human, porcine, bovine, equine, avian, piscine, etc.), bovine connective tissue, and/or other extracellular matrix proteins, for example. Bovine subdermal connective tissue may be harvested using sterile techniques and/or may be formed in a sterile mold, for example in a cylindrical shape, among other shapes described herein.

While operations may be depicted in the drawings in an order, this should not be understood as requiring that such operations be performed in the particular order shown and/or in sequential order, and/or that all illustrated operations be performed, to achieve useful outcomes.

Examples of the subject matter described in this specification have been described. The actions recited in the claims can be performed in a different order and still achieve useful outcomes, unless expressly noted otherwise. For example, the processes depicted in the accompanying figures do not require the particular order shown, and/or sequential order, to achieve useful outcomes. Multitasking and parallel processing may be advantageous in one or more scenarios.

While the present disclosure has been illustrated and described in detail in the drawings and foregoing description, the same is to be considered as illustrative and not restrictive in character, it being understood that only certain examples have been shown and described, and that all changes and modifications that come within the spirit of the present disclosure are desired to be protected.

What is claimed is:

1. An implant device configured to repair tissue, the device comprising:

a distal end, the distal end configured to be connectable by a plurality of sutures to at least a first part of the tissue;

a proximal end opposite the distal end along a longitudinal axis, the proximal end configured to be connectable by the plurality of sutures to at least a second part of the tissue;

a collagen substrate configured to form a connection between the first part of the tissue and the second part of the tissue, immobilize autologous blood between the first and second parts of the tissue, and form and maintain a clot between the first and second parts of the tissue when autologous blood is absorbed by the collagen substrate and the collagen substrate is positioned between first and second parts of the tissue; and a plurality of preformed channels in the substrate that extend along or at an angle with respect to the longitudinal axis, the substrate defining a first opening at an end of each preformed channel of the plurality of preformed channels, and a second opening in the substrate at an opposite end of each pre-formed channel of the plurality of preformed channels relative to the first opening, wherein a first suture of the plurality of sutures is preloaded at least partially within a first preformed channel of the plurality of preformed channels, and wherein a second suture of the plurality of sutures is preloaded at least partially within a second preformed channel of the plurality of preformed channels.

2. The device of claim 1, wherein the device further comprises at least one suture preloaded at least partially within one preformed channel of the plurality of preformed channels.

3. The device of claim 1, wherein the device is configured such that the tissue is at least one of: soft tissue, a tendon, or a ligament.

4. The device of claim 1, wherein the collagen substrate further comprises bovine connective tissue.

5. The device of claim 1, wherein the device has at least one of: a substantially cylindrical shape, a substantially oval shape, a substantially round shape, a substantially rectangular shape, a substantially square shape, or a substantially trapezoidal shape.

6. The device of claim 1, wherein the substrate is constructed of one or more materials saturable by human blood.

7. The device of claim 1, wherein each preformed channel of the plurality of preformed channels is formed in at least one of: during a formation of the device, or proximate in time to a post-formation processing of the device.

8. The device of claim 2, wherein the at least one suture is at least one of: an absorbable suture, or a non-absorbable suture.

9. The device of claim 1, wherein the plurality of preformed channels comprises:

a first preformed channel;

a second preformed channel;

a third preformed channel; and a fourth preformed channel.

10. The device of claim 9, further comprising:

a first suture preloaded at least partially within the first preformed channel;

a second suture preloaded at least partially within the second preformed channel;

a third suture preloaded at least partially within the third preformed channel; and a fourth suture preloaded at least partially within the fourth preformed channel.

11. The device of claim 10, wherein the device is further configured such that:

the first suture passes through the first and second openings of the first preformed channel;

the second suture passes through the first and second openings of the second preformed channel;

the third suture passes through the first and second openings of the third preformed channel; and the fourth suture passes through the first and second openings of the fourth preformed channel.

12. The device of claim 9, wherein the device is further configured such that:

the first and second openings of the first preformed channel in the substrate are each disposed in a first quadrant of the proximal end at a penetration angle ranging between zero to forty-five degrees relative to the longitudinal axis;

the first and second openings of the second preformed channel in the substrate are each disposed in a second quadrant of the proximal end at a penetration angle ranging between zero to forty-five degrees relative to the longitudinal axis;

the first and second openings of the third preformed channel in the substrate are each disposed in a third quadrant of the proximal end at a penetration angle ranging between zero to forty-five degrees relative to the longitudinal axis; and the first and second openings of the fourth preformed channel in the substrate are each disposed in a fourth quadrant of the proximal end at a penetration angle ranging between zero to forty-five degrees relative to the longitudinal axis.

13. The device of claim 1, wherein at least one preformed channel of the plurality of preformed channels is further configured such that:

the first opening is disposed in the proximal end at a penetration angle ranging between zero to forty-five degrees relative to the longitudinal axis; and the second opening is disposed in the distal end at a penetration angle ranging between zero to forty-five degrees relative to the longitudinal axis.

14. The device of claim 9, wherein the device is further configured such that at least one of: the first preformed channel, the second preformed channel, the third preformed channel, or the fourth preformed channel has a trajectory within the substrate that is at least one of: substantially straight, substantially diagonal, or substantially spiral.

15. The device of claim 1, wherein the plurality of preformed channels comprises a first preformed channel, and a second preformed channel.

16. The device of claim 15, wherein the device is further configured such that:

the first and second openings of the first preformed channel in the substrate are each disposed in a first half of the proximal end at a penetration angle ranging between zero to forty-five degrees relative to the longitudinal axis; and the first and second openings of the second preformed channel in the substrate are each disposed in a second half of the proximal end at a penetration angle ranging between zero to forty-five degrees relative to the longitudinal axis.

17. A method of repairing a subject's tissue with an implant device, the method comprising:

tensioning a first preloaded suture at least partially disposed within a first preformed channel of a plurality of preformed channels of the implant device, the first preformed channel disposed along a longitudinal axis of the implant device from a proximal end opposite a distal end and configured to accommodate transmission of the first preloaded suture through the first preformed channel;

tensioning a second preloaded suture at least partially disposed within a second preformed channel of a plurality of preformed channels of the implant device, the second preformed channel disposed along the longitudinal axis of the implant device from the proximal end opposite the distal end and configured to accommodate transmission of the second preloaded suture through the second preformed channel;

connecting the distal end of the implant device to at least a first part of the tissue via a first length of the first preloaded suture extending from the first preformed channel at the distal end and via a second length of the second preloaded suture extending from the second preformed channel at the distal end; and connecting the proximal end of the implant device to at least a second part of the tissue via a second length of the first preloaded suture extending from the first preformed channel at the proximal end and via a second length of the second preloaded suture extending from the second preformed channel at the proximal end, the distal end and the proximal end being connected by a substrate of the implant device, the substrate configurable to immobilize autologous blood between the first and second parts of the tissue and form and maintain a clot between the first and second parts of the tissue.

18. The method of claim 17, further comprising: saturating the substrate with the subject's blood.

19. The method of claim 17, wherein the subject's tissue is at least one of: a soft tissue, a tendon, or a ligament.

20. The method of claim 17, wherein at least one the first preloaded suture or the second preloaded suture is an absorbable suture, or a non-absorbable suture.

21. The method of claim 17, wherein the substrate comprises bovine connective tissue.

22. The method of claim 17, wherein the implant device has at least one of: a substantially cylindrical shape, a substantially oval shape, a substantially round shape, a substantially rectangular shape, a substantially square shape, or a substantially trapezoidal shape.

23. The method of claim 17, wherein each preformed channel of the plurality of preformed channels is formed at least one of: during a formation of the device, or proximate in time to a post-formation processing of the device.

24. The method of claim 17, wherein the substrate is porous.

25. The method of claim 17, wherein the clot releases at least one of: healing growth factors or proteins.

26. The method of claim 17, wherein the substrate comprises collagen.

27. An implant device for repairing a subject's tissue, the implant device comprising:

a first preloaded suture at least partially disposed within a first preformed channel of a plurality of preformed channels of the implant device, the first preformed channel disposed along a longitudinal axis of the implant device from a proximal end opposite a distal end and configured to accommodate tensioning and transmission of the first preloaded suture through the first preformed channel;

a second preloaded suture at least partially disposed within a second preformed channel of the plurality of preformed channels of the implant device, the second preformed channel disposed along the longitudinal axis of the implant device from the proximal end opposite the distal end and configured to accommodate tensioning and transmission of the second preloaded suture through the second preformed channel;

wherein the distal end of the implant device is connectable to at least a first part of the tissue via a first length of the first preloaded suture extending from the first preformed channel at the distal end and via a second length of the second preloaded suture extending from the second preformed channel at the distal end; and wherein the proximal end of the implant device is connectable to at least a second part of the tissue via a second length of the first preloaded suture extending from the first preformed channel at the proximal end and via a second length of the second suture extending from the second preformed channel at the proximal end, a substrate of the implant device being disposed between the distal end and the proximal end, the substrate configured to immobilize autologous blood between the first and second parts of the tissue and form and maintain a clot between the first and second parts of the tissue.

28. The device according to claim 27, further comprising: saturating the substrate with the subject's blood.

29. The device according to claim 27, wherein the subject's tissue is at least one of a soft tissue, tendon, or a ligament.

30. The device according to claim 27, wherein at least one of the first preloaded suture or the second preloaded suture is an absorbable suture, or a non-absorbable suture.

31. The device according to claim 27, wherein the substrate comprises bovine connective tissue.

32. The device according to claim 27, wherein the implant device has at least one of a substantially cylindrical shape, a substantially oval shape, a substantially round shape, a substantially rectangular shape, asubstantially square shape, or a substantially trapezoidal shape.

33. The device according to claim 27, wherein each preformed channel of the plurality of preformed channels is formed at least one of: during a formation ofthe device, or proximate in time to a post-formation processing of the device.

* * * * *